US006228891B1

(12) United States Patent
Enzmann et al.

(10) Patent No.: US 6,228,891 B1
(45) Date of Patent: May 8, 2001

(54) USE OF 2,3-DIMETHOXY-5-METHYL-6-DECAPRENYL-1,4-BENZOQUINONE

(75) Inventors: Franz Enzmann, Bad Homburg (DE); Burkhard Lachmann, Rotterdam (NL)

(73) Assignee: MSE Pharmazeutika GmbH, Bad Homburg (DE)

( * ) Notice: Subject to any disclaimer, the term of this patent is extended or adjusted under 35 U.S.C. 154(b) by 0 days.

(21) Appl. No.: 09/355,932

(22) PCT Filed: Feb. 11, 1998

(86) PCT No.: PCT/EP98/00743

§ 371 Date: Oct. 12, 1999

§ 102(e) Date: Oct. 12, 1999

(87) PCT Pub. No.: WO98/35658

PCT Pub. Date: Aug. 20, 1998

(30) Foreign Application Priority Data

Feb. 12, 1997 (DE) ............................................. 197 05 232

(51) Int. Cl.$^{7}$ ........................... A61K 31/12; A61K 35/42
(52) U.S. Cl. ............................................ 514/690; 424/557
(58) Field of Search ............................. 514/690; 424/557

(56) References Cited

U.S. PATENT DOCUMENTS

| | | | | |
|---|---|---|---|---|
| 4,654,373 | * | 3/1987 | Bertelli | 514/690 |
| 4,824,669 | | 4/1989 | Folkers et al. | 424/94.1 |
| 5,451,569 | | 9/1995 | Wong et al. | 514/3 |
| 5,912,272 | * | 6/1999 | Hoppe et al. | 514/678 |

FOREIGN PATENT DOCUMENTS

| | | |
|---|---|---|
| 2184355A | 6/1987 | (GB) . |
| 63-036789 | 2/1988 | (JP) . |

OTHER PUBLICATIONS

Reynolds, *Martindale The Extra Pharmacopoeia* Thirty–First Edition, p. 1764: Ubidecarenone (1996).

* cited by examiner

*Primary Examiner*—Theodore J. Criares
(74) *Attorney, Agent, or Firm*—Jacobson, Price, Holman & Stern, PLLC

(57) ABSTRACT

2,3-Dimethoxy-5-methyl-6-decaprenyl-1,4-benzoquinone can be used for the topical and oral treatment of diseases of the skin and the mucosae of the mouth, the stomach, the bowels, the vagina and the lung.

4 Claims, No Drawings

USE OF 2,3-DIMETHOXY-5-METHYL-6-DECAPRENYL-1,4-BENZOQUINONE 2,3-Dimethoxy-5-methyl-6-decaprenyl-1,4-benzoquinone is also known by the designation of coenzyme Q10. This substance plays a role in the respiratory chain and, in addition, is an anti-oxidant which is capable of scavenging free radicals, which are transmitted by vitamins, in particular. In addition, Q10 determines the elasticity and dynamics of cell membranes. Therefore, it is recommended as a monopreparation and in combination with other active substances for oral administration. For skin care, it is additionally offered in the form of a liposome cream which allows the active ingredient to penetrate through the horny layer barrier and then to accumulate in the various strata of the skin. The liposome cream used to date has been prepared on the basis of lecithins, forming a lipid bilayer around an aqueous interior space. Q10 deposits inside the membrane.

It has now been found that this substance is suitable, to a much larger extent than has been known and predictable to date, for the topical or oral treatment of diseases of the cardiovascular system, the lung, the muscles, the stomach and bowels (ulcer and gastritis), the skin, the nerves, in degenerative metabolic imbalance, incontinence, periodontosis, mitochondrial diseases, immune deficiency and rheumatism, and for the treatment of cerebral paresis, glycogenosis, tinnitus, incontinence, rheumatic arthritis, asthma, IRDS and ARDS, diabetic neuropathy, and diseases of the skin and mucosae (mouth, stomach, bowels, vagina and lung). In particular, it is suitable for the treatment of acne, psoriasis, neurodermitis, burns, radiolesions, eczemas, wounds, ulcus cruris, cancer of the skin, skin ageing, anus, periodontitis, ulcer, gastritis and rheumatism.

For oral application, it may be employed in the form of powders in hard gelatin capsules or in an oily suspension in soft gelatin capsules. Applicant distributes such a monopreparation with 30 mg of the active substance and, if required by the physician, with 120 mg of Q-10.

For topical application, the active substance can be employed in the form of special liposome formulations. Liposomes are tiny spherical items consisting of lipid layers and an aqueous interior space. The layers are generated by suitably mixing the active ingredient with emulsifiers, such as lecithin. Q10 will then directly deposit within the lipid bilayers, dynamizing them.

Instead of the liposome cream used to date, there may also be employed a cream which additionally contains an effective amount of pulmonary surfactant. Liposomes based on pulmonary surfactant are only monolayered, in contrast to the bilayered liposomes of lecithin. These liposomes are capable to penetrate into the skin even faster and in a more intense way. Thus, surprisingly, the combination of conventional liposomes and pulmonary surfactant proved to be still more effective.

Pulmonary surfactant can be isolated from the lungs; it is a complex of special phospholipids, neutral lipids and surfactant proteins which together form a monolayered barrier between the air and the liquid surface of the lung. Pulmonary surfactant is produced in the alveolar type II cells from which it is released into the alveolar space. Pulmonary surfactant may also be recombined from its components.

To date, pulmonary surfactant has only been employed for instillation in diseases or deficiencies of the lung.

Other applications have not been considered to date. It has now been found unexpectedly that pulmonary surfactant is capable of penetrating into the outer skin and the mucosa of the gastrointestinal region, the oral and vaginal regions, i.e., either alone or in combination with liposomes.

It is of minor importance whether highly purified or less highly purified pulmonary surfactant preparations from a wide variety of species or recombined pulmonary surfactant are employed (pig, cow, sheep, etc.). Less highly purified preparations have the advantage of a low-cost production.

Thus, pulmonary surfactant is suitable for improving the efficiency of 2,3-dimethoxy-5-methyl-6-decaprenyl-1,4-benzoquinone and for accelerating the onset of activity. Although pulmonary surfactant is physiologically released from the lung tissue, it is surprisingly capable of increasing the absorption of pulmonary surfactant and Q10 into the tissues. This particularly applies to the now found further indications for the application of 2,3-dimethoxy-5-methyl-6-decaprenyl-1,4-benzoquinone in the treatment of diseases of the skin and the mucosae of the mouth, the stomach and the bowels as well as the vagina.

The effectiveness of Q10 alone and in combination with pulmonary surfactant in the treatment of tinnitus, incontinence, glycogenosis, cerebral paresis in children, arthritis, rheumatism, neurodermitis, psoriasis and diabetic neuropathy is completely novel. In addition, Q10, in combination with pulmonary surfactant, contributes to an improved treatment of diseases of the cardiovascular system, the muscles, the lung, the nerves and the immune system.

What is claimed is:

1. A method for treating diseases of the skin and of the mucosa of the mouth, stomach, bowels, vagina, and lungs, comprising administering to a patient in need thereof a medicament comprising a) an effective amount of 2,3-dimethoxy-5-methyl-6-decaprenyl-1,4-benzoquinone, in combination with b) an effective amount of a pulmonary surfactant.

2. The method of claim 1, wherein the disease is psoriasis, neurodermitis, burns, radiolesions, wounds, ulcus cruris, eczema, cancer of the skin, or skin ageing.

3. The method of claim 1, wherein the pulmonary surfactant is a raw extract.

4. The method of claim 1, wherein the medicament is a liposome formulation.

* * * * *